US006620808B2

(12) United States Patent
Van Der Klish et al.

(10) Patent No.: US 6,620,808 B2
(45) Date of Patent: *Sep. 16, 2003

(54) ENDOCRINE MODULATION WITH POSITIVE MODULATORS OF AMPA TYPE GLUTAMATE RECEPTORS

(75) Inventors: Peter Van Der Klish, Laguna Beach, CA (US); Gary Lynch, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/964,288

(22) Filed: Sep. 25, 2001

(65) Prior Publication Data

US 2002/0045612 A1 Apr. 18, 2002

Related U.S. Application Data

(63) Continuation of application No. 08/853,221, filed on May 9, 1997, now Pat. No. 6,329,368.

(51) Int. Cl.[7] ...................... A61K 31/54; A61K 31/535; A61K 31/55
(52) U.S. Cl. ................................ 514/223.2; 514/230.2; 514/212
(58) Field of Search ........................... 514/223.2, 230.2, 514/212

(56) References Cited

U.S. PATENT DOCUMENTS

| | | | | | |
|---|---|---|---|---|---|
| 5,459,138 A | * | 10/1995 | Pirotte et al. | ............ | 514/222.8 |
| 5,792,764 A | * | 8/1998 | Pirotte et al. | ............ | 514/222.8 |
| 5,852,008 A | | 12/1998 | Lynch et al. | | |
| 6,329,368 B1 | | 12/2001 | Van Der Klish | | |

FOREIGN PATENT DOCUMENTS

| | | |
|---|---|---|
| WO | WO 96 38414 | 12/1996 |
| WO | WO 97 07799 | 3/1997 |
| WO | WO 97 26884 | 7/1997 |
| WO | WO 97 39750 | 10/1997 |

OTHER PUBLICATIONS

Pinella et al., "Positive Role of Non–N–Methyl–D–Aspartate Receptors in the Control of Growth Hormone Secretion in Male Rats" (1996) J. Endocrinol. Invest., 19, 353–358.*
Tena–Sempere et al., "Involvement of Endogenous Nitric Oxide in the Control of Pituitary Responsiveness to Different Elicitors of Growth Hormone in Perpubertal Rats" (1996) Neruoendocrinology, 64(2), 146–152.*
Palmer, et al., "Comparison Of The Effects Of An Ampakine With Those Of Methamphetamine On Aggregate Neuronal Activity In Cortex Versus Striatum," *Molecular Brain Res.* (Jun. 1997) vol. 46:127–135.

Lynch et al. International Clinical Psychopharmacology, 11:13–19, 1996.
Lees, CNS Drugs, 5:51–74, 1996.
Johnson et al. Exp. Brain Res., 59:57–61, 1985.
Tsuzuki et al. Molecular Brain Research, 16:105–110, 1992.
Ingvar et al. "Enchancement By an Ampakine Of Memory Encoding in Humans," *Experimental Neurology* (1997) vol. 146:553–559.
Brann et al. (1993) "Role of non–NMDA receptor neurotransmission in steroid and preovulatory gonadotropin surge expression in the female rat," *Mol. Cell. Neurosci.* 4:292–297.
Crew et al. (1987) "Age–related decrease of growth hormone production and prolactin gene expression in the mouse pituitary," *Endocrinology* 121: 1251–1255.
Donoso et al. (1990) "Glutamate receptors of the non–NMDA types mediate the increase in Luteinizing Hormone–Releasing Hormone release by excitatory amino acids," *Endocrinology* 126:414–420.
Gore et al. (1994) "Regulation of GnRH gene expression by the excitatory amino acids kainic acid and NMDA in the male rat," *Endocrinology* 134:2026–2031.
Lopez et al. (1992) "Endogenous excitatory amino acids and glutamate receptor subtypes involved in the control of hypothalamic luteinizing hormone–releasing hormone secretion," *Endocrinology* 130:1986–1992.
Ping et al. (1994) "A physiological role for N–methyl–D–aspartic acid and non–N–methyl–D–aspartic acid receptors in pulsatile gonadotropin secretion in the adult female rat," *Endocrinology* 135:113–118.
Grazia, Maria et al., "Growth Hormone and Somatostain Gene Expression in Adult and Aging Rats as Measured by Quantitative in situ Hybridization[1]," *Neuroendocrinology* (1991) vol. 54: 607–615.
Nissen, R., et al., "Regulation of Spontaneous Phasic Firing of Rat Supraoptic Vasopressin Neurones in vivo By Glutamate Receptors," *Journal of Physiology* (1995) vol. 484: 415–424.
Parker, Steven et al., "Stimulation of Oxytocin Release in the Lactating Rat by Central Excitatory Amino Acid Mechanisms: Evidence for Specific Involvement of R, S–a–Amino–3–Hydroxy–5–Methylisoxazole–4–Propionic Acid–Sensitive Glutamate Receptors," *Endocrinology* (1993) vol. 133(6): 2847–2854.

* cited by examiner

*Primary Examiner*—Jon P. Weber
(74) *Attorney, Agent, or Firm*—Paula A. Borden; Bret E. Field; Boziceivic, Field & Francis, LLP (57) ABSTRACT

Methods for modulating the endocrine system of a mammal are provided. In the subject methods, a positive allosteric modulator of AMPA receptors of the hypothalamus are administered to the host. The subject methods find use in applications where it is desired to increase the circulatory level of a hormone in a mammalian host, such as diseased states characterized by abnormally depressed circulatory levels of the hormone.

8 Claims, 3 Drawing Sheets

ENDOCRINE MODULATION WITH POSITIVE MODULATORS OF AMPA TYPE GLUTAMATE RECEPTORS

FIELD OF THE INVENTION

The field of this invention is modulation of mammalian endocrine systems.

BACKGROUND OF THE INVENTION

The mammalian endocrine system is critical to mammalian cell-cell communication. In the endocrine system, hormones are secreted by endocrine glands into the circulatory system and adsorbed onto specific receptors, usually located distal to the site of secretion. The endocrine system is used by mammals to orchestrate a variety of different physiological processes, including metabolism, growth and maturation, circadian cycles and the like.

An important member of the endocrine system is the hypothalamic-pituitary axis. In general, this member of the endocrine system has two components: 1) a magnocellular (large cell) system which releases the hormones oxytocin and vasopressin (arginine vasopressin, AVP) directly into the blood stream from axon terminals located in the posterior pituitary and 2) a parvocellular (small cell) system that secretes small peptides called releasing factors which enter fenestrated capillaries, descend through the hypophyseal portal veins, and then diffuse through additional fenestrated capillaries to individual cells of the anterior pituitary. Principal neuropeptides secreted by the hypothalamus include growth hormone releasing hormone (GHRH), growth hormone release-inhibiting hormone (somatostatin), prolactin release inhibitory factor (dopamine), gonadotropin-releasing hormone (GnRH), corticotropin-releasing hormone (CRH), and thyrotropin-releasing hormone (TRH). Hormones released by the pituitary in response to hypothalamus neuropeptide influence include growth hormone (GH), prolactin (PRL), follicle-stimulating hormone (FSH), luteinizing hormone (LH), adrenocorticotropic hormone (ACTH, corticotropin) and thyrotropin (thyroid stimulating hormone, TSH).

Figure 1:
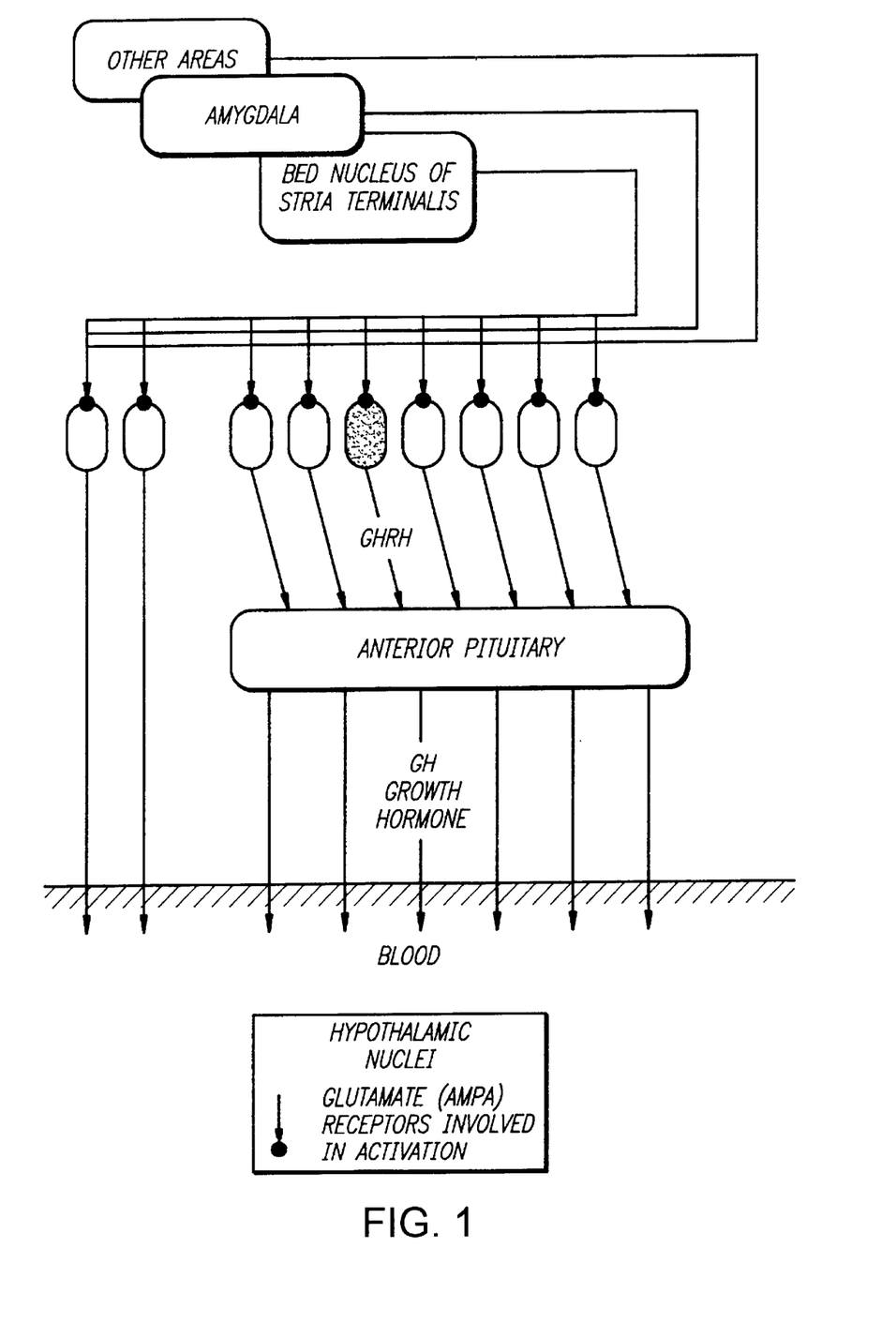
FIG. 1 provides a schematic diagram showing the various diverse influences on the magnocellular and parvocellular secretory regions of the hypothalamus.

The magnocellular and parvocellular secretory regions of the hypothalamus receive strong inputs from a variety of regions including other segments of the hypothalamus, diverse areas of the brain stem, and from forebrain (telencephalic) structures. See FIG. 1. Prominent in the last group are projections from the limbic system including the central and medial divisions of the amygdala and the closely related bed nucleus of the stria terminals.

Abnormalities in endocrine or hormonal systems, e.g. hypo- or hypersecretion of one or more particular hormones, can have a profound affect on the ability of a mammal to function. For example, hypersecretion of pituitary hormones can result in a number of different diseased states, including: Cushing's syndrome (ACTH), acromegaly and gigantism (GH), and the like. Hyposecretion of pituitary hormones is also implicated in a number of diseased states, including dwarfism (GH), Sheehan's syndrome (panhypopituitarism), and the like.

Recently, age dependent dysfunction of hormonal systems has been postulated to be associated with the mammalian aging process. For example, GH blood levels in the elderly are lower than GH blood levels in younger populations, where lower GH blood levels have been theorized to be associated with symptoms of the aging process, such as decreases in lean body mass, muscle and bone.

Current methods of treating diseases associated with endocrine system dysfunction involving the hyposecretion of one or more particular hormones have centered on direct hormonal replacement, e.g. synthetic or recombinant growth hormone for GH deficient youths. While such approaches can be successful, hormone replacement therapy can be associated with a number of different disadvantages, such as risk of pathogen transmission, delivery, over compensation of replacement hormone, and the like.

As such, there continues to be an interest in the development of new methods of treating diseases characterized by endocrine system dysfunction. Of particular interest is the identification of small molecules which have a modulatory effect in the amount of endogenous hormone production, and methods of using such molecules in the regulation of hormonal circulatory levels.

RELEVANT LITERATURE

References describing the presence and distribution of AMPA type glutamate receptors in the hypothalamus include: Aubry et al., (1996) "Expression of ionotropic receptor subunit mRNAs by paraventricular corticotropin-releasing factor (CRF) neurons," *Neurosci. Lett.* 205:95–98; Van den Pool et al. (1994) "Ionotropic glutamate receptor gene expression in the hypothalamus: Localization of AMPA, kainate and NMDA receptor mRNA with in situ hybridization," *J. Comp. Neurology* 343:428–444; Brann (1995) "Glutamate: a major excitatory transmitter in neuroendocrine regulation. *Neuroendocrinology* 61:213–225; Ginsberg et al. (1995) "The AMPA glutamate receptor GluR3 is enriched in oxytocinergic magnocellular neurons and is localized at synapses," *Neuroscience* 65:564–575.

References describing the effects of AMPA receptor agonists on the excitation of hypothalamic neurons and on the release of releasing factors include: Nissen et al. (1995), "Regulation of spontaneous phasic firing of rat supraoptic vasopressin neurons in vivo by glutamate receptors," *J. Physiol.* 484:415–424; Donoso et al. (1990) "Glutamate receptors of the non-NMDA types mediate the increase in Luteinizing Hormone-Releasing Hormone release by excitatory amino acids," *Endocrinology* 126:414–420; Lopez et al. (1992) "Endogenous excitatory amino acids and glutamate receptor subtypes involved in the control of hypothalamic luteinizing hormone-releasing hormone secretion," *Endocrinology* 130:1986–1992; Parker and Crowley (1993) "Stimulation of oxytocin release in the lactating rat by central excitatory amino acid mechanisms: evidence for specific involvement of AMPA sensitive glutamate receptors," *Endocrinology* 133:2847–2854; Brann et al. (1993) "Role of non-NMDA receptor neurotransmission in steroid and preovulatory gonadotropin surge expression in the female rat," *Mol. Cell. Neurosci.* 4:292–297; Ping et al. (1994) "A physiological role for N-methyl-D-aspartic acid and non-N-methyl-D-aspartic acid receptors in pulsatile gonadotropin secretion in the adult female rat." *Endocrinology* 135:113–118.

References studying the influence of glutamate receptor agonists on gene expression of hypothalamic factors include: Gore and Roberts (1994) "Regulation of GnRH gene expression by the excitatory amino acids kainic acid and NMDA in the male rat," *Endocrinology* 134:2026–2031. References describing age associated changes in the production of pituitary hormones include: Crew et al. (1987) "Age-related decrease of growth hormone production and prolactin gene expression in the mouse pituitary," *Endocrinology* 121:1251–1255; Martinoli et al.

(1991) "Growth hormone and somatostatin gene expression in adult and aging rats as measured by quantitative in situ hybridization," *Neuroendocrinology* 57:607–615.

SUMMARY OF THE INVENTION

Methods for modulating mammalian endocrine systems are provided. In the subject methods, allosteric modulators of AMPA receptors of the hypothalamus, e.g. agents belonging to the "ampakine" family of compounds, are administered to the host. The subject methods find use in a variety of different applications where modulation of the endocrine system of a mammal is desired, such as in the treatment of diseases associated with hormonal system dysfunction, particularly with abnormally decreased circulatory levels of a hormone, e.g. growth hormone, resulting from down regulation in endogenous hormonal production.

It is an object of the invention to treat hormonal imbalances. Another object of the invention is to show the effects of aging related to decreases in hormonal levels which normally occur with aging.

An advantage of the invention is that a host's endogenous hormones are used.

A feature of the invention is that formulations with specific positive modulators of AMPA type glutamate receptors are employed.

These and other objects, advantages, and features of the invention will become apparent to those persons skilled in the art upon reading the details of the subject invention, as more fully described below.

DESCRIPTION OF THE SPECIFIC EMBODIMENTS

Methods of modulating the endocrine system of a mammalian host are provided. In the subject methods, a therapeutically effective amount of an agent or positive modulator which enhances the effect of excitatory amino acid transmitters on the AMPA type glutamate receptor and which crosses the blood-brain barrier, e.g. a compound belonging to the ampakine family of compounds, is administered to a mammalian host. The subject methods find use in a variety of applications where regulation of the mammalian endocrine system is desired, such as in the treatment of diseases associated with abnormally low circulatory levels of a hormone, where the low hormonal levels are the result of down regulation of hormone secreting tissue, erg. endocrine glands.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an" and "the" include plural reference unless the context clearly dictates otherwise. Unless defined otherwise all technical and scientific terms used herein have the same meaning as commonly understood to one of ordinary skill in the art to which this invention belongs.

In the subject methods, an ampakine or other blood brain permeable positive modulator of AMPA receptors is administered to a mammalian host to modulate the activity of the endocrine system of the mammalian host. Compounds suitable for use in the subject methods are generally those which amplify (up-modulate) the activity of the natural stimulators of AMPA receptors, particularly by amplifying excitatory synaptic responses. Compounds suitable for use may be identified by the following assay which measures enlargement of the excitatory postsynaptic potential (EPSP) in in vitro brain slices, such as rat hippocampal brain slices.

In this assay, slices of hippocampus from a mammal such as rat are prepared and maintained in an interface chamber using conventional methods. Field EPSPs are recorded in the stratum radiatum of region CA1b and elicited by single stimulation pulses delivered once per 20 seconds to a bipolar electrode positioned in the Schaffer-commissural projections (see Granger, R et al., 1993, *Synapse*, 15:326–329; Staubli, U. et al., 1994a, *Proc. Natl. Acad. Sci.*, 91:777–781; and Staubli, U. et al., 1994b, *Proc. Natl. Acad Sci.*, 91:11158–11162; Arai, A. et al., 1994, *Brain Res.*, 638:343–346; Arai, A. et al. 1996a, Neuroscience 75:573–585, and Arai et al., 1996b, J. Pharm. Exp. Ther. 278:627–638.

The wave form of a normal monosynaptic response is composed of:

an AMPA component, which has a relatively rapid rise time in the depolarizing direction (about 5–10 msec) and which decays within about 20 msec;

an NMDA component (slow rise time of about 30–40 msec and slow decay of about 40–70 msec)—the NMDA portion will not appear in normal CSF media, due to the voltage requirement for NMDA receptor channel activation, but in low magnesium media, an NMDA component may appear; and a GABA component in the opposite (hyperpolarizing) direction as the glutamatergic (AMPA and NMDA) components, exhibiting a time course with a rise time of about 10–20 msec and very slow decay (about 50–100 msec or more).

The different components can be separately measured to assay the effect of a putative AMPA receptor enhancing agent. This is accomplished by adding agents that block the unwanted components, so that the detectable responses are essentially only AMPA responses. For example, to measure AMPA responses, an NNMA receptor blocker (for example, AP-5 or other NMDA blockers known in the art) and/or a GABA blocker (for example, picrotoxin or other GABA blockers known in the art) are added to the slice. To prevent epileptiform activity in the GABA-blocked slices, known agents such as tetrodotoxin may be used.

AMPA up-modulators useful in the present invention are substances that cause an increased ion flux through the AMPA receptor complex channels in response to glutamatergic stimulation. Increased ion flux is typically measured as one or more of the following non-limiting parameters: at least a 10% increase in decay time, amplitude of the waveform and/or the area under the curve of the waveform and/or a decrease of at least 10% in rise time of the waveform, for example in preparations treated to block NMDA and GABA components. The increase or decrease is preferably at least 25–50%; most preferably it is at least 100%. How the increased ion flux is accomplished (for example, increased amplitude or increased decay time) is of secondary importance; up-modulation is reflective of increased ion fluxes through the AMPA channels, however achieved.

An additional and more detailed assay is that of excised patches, ie., membrane patches excised from cultured hippocampal slices; methods are described in Arai et al., 1994. Outside-out patches are obtained from pyramidal hippocampal neurons and transferred to a recording chamber. Glutamate pulses are applied and data are collected with a patch clamp amplifier and digitized (Arai et al., 1994, 1996a,b). Because no GABA is applied to the patch, GABAergic currents will not be elicited. Any NMDA currents can be blocked as above (for example, with AP-5).

The central action of a compound can be verified by measurement of synaptic responses or the overall activity of brain cells in behaving animals (see Staubli et al., 1994a) and time course of biodistribution can be ascertained via injection and subsequent quantitation of drug levels in various tissue samples. Quantitation can be accomplished by methods known to those skilled in the art and will vary depending on the chemical nature of the drug.

Compounds useful in the practice of this invention are generally those that amplify the activity of the natural stimulators of AMPA receptors, particularly by amplifying excitatory synaptic response as defined above. They are quite varied in structure and so long as they embrace the above physiological properties and cross the blood brain barrier, they will work in this invention. Preferred compounds include, but are not limited to, compounds identifiable by the assays described above.

A class of preferred compounds useful in the practice of this invention are those having the formula In this formula:
$R^1$ is N or CH.
m is 0 or 1.
$R^2$ is $(CR^3{}_2)_{n-m}$ or $C_{n-m}R^3{}_{2(n-m)-2}$, in which n is 4, 5, or 6, and the $R^3$'s in any single compound are the same or different.
Each $R^3$ is H or $C_1$–$C_6$ alkyl, or
one $R^3$ is combined with $R^4$ to form a single bond linking the no. 6 and no. 3' ring vertices or to form a single divalent linking moiety linking the no. 6 and no. 3' ring vertices, any remaining $R^3$'s being H or $C_1$–$C_6$ alkyl, or
one $R^3$ is combined with $R^5$ to form a single bond linking the no. 2 and no. 3' ring vertices or to form a single divalent linking moiety linking the no. 2 and no. 3' ring vertices, any remaining $R^3$'s being H or $C_1$–$C_6$ alkyl.

The "linking moiety" in the $R^3$ definitions is $CH_2$, O, NH or $N(C_1$–$C_6$ alkyl).

$R^4$ when not combined with any $R^3$ is H, $C_1$–$C_6$ alkyl, or $C_1$–$C_6$ alkoxy.

$R^5$ when not combined with any $R^3$ is H, $C_1$–$C_6$ alkyl, or $C_1$–$C_6$ alkoxy.

$R^6$ is H, OH, $C_1$–$C_6$ alkyl $C_1$–$C_6$ alkoxy, hydroxy-($C_1$–$C_6$ alkyl), or $C_1$–$C_6$ alkoxy-($C_1$–$C_6$ alkyl), or is combined with $R^7$.

$R^7$ is H, OH, $C_1$–$C_6$ alkyl $C_1$–$C_6$ alkoxy, hydroxy-($C_1$–$C_6$ alkyl), $C_1$–$C_6$ alkoxy-$C_1$–$C_6$ alkyl), amino, mono ($C_1$–$C_6$ alkyl)amino, or di($C_1$–$C_6$ alkyl)amino, or is combined with $R^6$.

$R^6$ and $R^7$ when combined form one of the following

In these formulas:
$R^8$ is O, NH or $N(C_1$–$C_6$ alkyl).
$R^9$ is O, NH or $N(C_1$–$C_6$ alkyl).
The $R^{10}$'s in any single compound are the same or different, and each $R^{10}$ is H or $C_1$–$C_6$ alkyl.
p is 1,2, or 3.
q is 1 or 2.
Certain subclasses within the generic formula are preferred.
For example, $R^2$ is preferably $(CHR^3)_{n-m}$ or $C_{n-m}HR^3{}_{2(n-m)-3}$, and preferably either $C_{n-m}H_{2(n-m)-1}R^3$ or $C_{n-m}H_{2(n-m)-3}R^3$. Particularly preferred groups are $C_5H_9R^3$ and $C_5H_8$. Values of n equal to 4 or 5, and particularly 5, are preferred for compounds in which m is 0, while values of n equal to 3 or 4, and particularly 3, are preferred for compounds in which m is 1. The index m itself is preferably 0.

When one $R^3$ of an $R^2$ group is combined with $R^4$, the preferred combination is either a methylene ($CH_2$) group, an O atom, or a N atom, and most preferably an O atom. When one $R^3$ is combined with $R^5$, the preferred combination is similarly either a methylene ($CH_2$) group, an O atom, or a N atom, and most preferably an O atom. When no $R^3$'s are combined with either $R^4$ or $R^5$, preferred groups for $R^3$ are a H atom and a methyl group, with a H atom preferred. $R^3$'s that are not combined with either $R^4$ or $R^5$ are generally preferred.

$R^1$ is preferably N.

$R^4$ and $R^5$, when not combined with any $R^3$, are each preferably an H atom or a $C_1$–$C_6$ alkyl group, and more preferably an H atom or a methyl group. Among these, H and methyl are more preferred, and H is the most preferred. A preferred alkoxy group for both $R^4$ and $R^5$ is methoxy.

For $R^6$ and $R^7$, it is preferred that one of these groups is other than H. When not combined with each other to form one of the four divalent groups shown above, $R^6$ and $R^7$ are preferably chosen such that one is H and the other is OH, $C_1$–$C_6$ alkyl, $C_1$–$C_6$ alkoxy, hydroxy-($C_1$–$C_6$ alkyl), $C_1$–$C_6$ alkoxy-($C_1$–$C_6$ alkyl), amino, mono($C_1$–$C_6$ alkyl)amino, or di($C_1$–$C_6$ alkyl)amino. Among the latter list, preferred members are $C_1$–$C_3$ alkyl, $C_1$–$C_3$ alkoxy, hydroxy-($C_1$–$C_3$ alkyl), $C_1$–$C_3$ alkoxy-($C_1$–$C_3$ alkyl), amino, mono($C_1$–$C_3$ alkyl) amino, or di($C_1$–$C_3$ alkyl)amino. Most preferred are methoxy, ethoxy, hydroxymethoxy, hydroxyethoxy, methoxymethyl, ethoxymethyl, amino, methylamino, and dimethylamino. When $R^6$ and $R^7$ are combined to form one of the four divalent groups whose formulas are shown above, preferred among the four are the last two divalent groups, with the last divalent group particularly preferred. It is noted that the last divalent group forms an aromatic ring with two N atoms, fused to the phenyl ring shown in the generic formula.

For the divalent groups, $R^8$ is preferably an O atom. Likewise, $R^9$ is preferably an O atom. The $R^{10}$'s are preferably either H or methyl, independently, although in the most preferred compounds, all $R^{10}$'s are H atoms. Finally, p is preferably 1, and q is preferably 1 as well.

The terms "alkyl" and "alkoxy" are used herein to include branched-chain groups when containing three or more carbon atoms.

Compounds 1 through 25 below are examples of compounds within the scope of the generic formula and these definitions:

1

2

3

-continued

4

5

6

7

8

9 aniracetam

21

22

23

24

25

Compounds within the scope of this invention can be prepared by conventional methods known to those skilled in organic synthesis.

Some of the compounds, for example, can be prepared from an appropriately substituted benzoic acid by contacting the acid under conditions suitable to activate the carboxy group for the formation of an amide. This is accomplished, for example, by activating the acid with the carbonyl diimidazole, or with a chlorinating agent such as thionyl chloride or oxalyl chloride to obtain the corresponding benzoyl chloride. The activated acid is then contacted with a nitrogen-containing heterocyclic compound under conditions suitable for producing the desired imide or amide. Alternatively, the substituted benzoic acid can be ionized by contact with at least two equivalents of base such as triethylamine in an inert solvent such as methylene chloride or alcohol-free chloroform, and the ionized benzoic acid can then be reacted with pivaloyl chloride or a reactive carboxylic acid anhydride such as trifluoroacetic anhydride or trichloroacetic anhydride, to produce a mixed anhydride. The mixed anhydride is then contacted with a nitrogen-containing heterocyclic compound to produce the desired imide or amide.

A further alternative to these methods, suitable for some of the compounds in Formula I, is to contact the appropriately selected 3,4-(alkylenedihetero)-benzaldehyde with ammonia to form an imine, then contacting the imine with benzoyloxycarbonyl chloride to form the benzoyloxycarbonyl imine. Suitable 3,4-(alkylenedihetero)-benzaldehydes include 3,4-(methylenedioxy)benzaldehyde, 3,4-(ethylenedioxy)-benzaldehyde, 3,4-(propylenedioxy) benzaldehyde, 3,4-(ethylidenedioxy)-benzaldehyde, 3,4-(propylenedithio)-benzaldehyde, 3,4-(ethylidenedithio)-benzaldehyde, 5-benzimidazole-carboxaldehyde, and 6-quinoxalinecarboxaldehyde. The benzoyloxycarbonyl imine is then contacted with a simple conjugated diene such as butadiene under cycloaddition reaction conditions, and then with a Lewis acid under conditions suitable for a Friedel-Crafts acylation. Examples of suitable conjugated dienes include butadiene, 1,3-pentadiene, and isoprene, and examples of suitable Lewis acids include $AlCl_3$ and $ZnCl_2$.

Still further compounds within the generic formula are prepared from 2,3-dihydroxy naphthalene. This starting material is reacted with 1,2-dibromoethane in the presence of base to produce an ethylenedioxy derivative of naphthalene, which is then reacted with an oxidizing agent such as potassium permanganate to produce 4,5-ethylenedioxyphthaldehydic acid. The latter is contacted with anhydrous ammonia to form an imine, which is then treated with a suitable carbonyl-activating agent such as dicyclohexylcarbodiimide under cyclization conditions to form an acyl imine. The acyl imine is then reacted with a simple conjugated diene to achieve cycloaddition.

Still further compounds within the generic formula can be prepared by contacting a α-halotoluic acid with at least two equivalents of an alkali salt of lower alcohol according to the Williamson ether synthesis to produce an ether linkage. The resulting alkoxymethylbenzoic acid is activated with carbonyldiimidazole, thionyl chloride, dicyclohexylcarbodiimide, or any other suitable activating agent, and reacted with a suitable amine to achieve a carboxamide linkage.

In an alternate to the scheme of the preceding paragraph, a formyl-substituted aromatic carboxamide is prepared by activation of an appropriate starting acid with a tertiary amine (for example, triethyl amine) plus an acid chloride (for example, pivaloyl chloride) to produce a mixed anhydride for coupling to a suitable amine. The formyl group is then reduced to an alcohol by a suitable reducing agent such as sodium borohydride. The alcohol is then converted to a leaving group which is replaceable by the alkali salt of an alcohol. The leaving group can be generated by reagents such as thionyl chloride, thionyl bromide, mineral acids such as hydrochloric, hydrobromic or hydroiodic acids, or the combined action of a tertiary amine plus either a suitable sulfonic anhydride or sulfonyl halide. Alternatively, the alcohol can be activated by removing the proton. This is achieved by the action of a strong base such as sodium hydride in an aprotic solvent such as dimethylformamide.

The resulting alkoxide is then reacted with a suitable alkyl halide or other alkyl compound with a suitable leaving group to produce the desired ether linkage.

Fused ring structures such as those in which $R^4$ or $R^5$ and one of the $R^3$'s of the formula are combined as a single linking group can be snthesized in the following manner. The carboxyl group of an appropriately substituted salicylic acid is activated with carbonyldiimidazole in dichloromethane, chloroform, tetrahydrofuran, or other anhydrous solvent. An aminoalkylacetal such as $H_2N(CH_2)_3CH(OCH_2CH_3)_2$ is then added. The resulting amide is treated with an aryl or alkyl sulfonic acid, trifluoroacetic.acid, or other strong acid, in a solvent of low basicity such as chloroform or dichloromethane, to cleave the acetal and cyclize the intermediate aldehyde with the amide nitrogen and the phenolic oxygen.

In all of these reaction schemes, the methods and reaction conditions for each of the individual reactions are well within the routine skill of, and will be readily apparent to, the synthesis chemist.

The above described genus and species of ampakine compounds represent two large groups of the diverse glutarnatergic compounds that may be used in the present invention. Additional arnpakine compounds, i.e. compounds that enhance the stimulation of α-amino-3-hydroxy-5-methyl-isoxazole-4-propionic acid ("AMPA") receptors, include: 7-chloro-3-methyl-3-4-dihydro-2H-1,2,4-benzothiadiazine S,S-dioxide, as described in Zivkovic et at, 1995, *J. Pharmacol. Exp. Therap.*, 272:300–309; Thompson et at, 1995, *Proc. Natl. Acad. Sci. USA*, 92:7667–7671; 3-bicyclo[2,2,1]hept-5-en-2-yl-6-chloro-3,4-dihydro-2H-1,2,4benzothiadiazine-7-sulfonamide 1,1-dioxide, as described in Yamada, et al., 1993, *J. Neurosc.* 13:3904–3915; and 7-fluoro-3-methyl-5-ethyl-1,2,4-benzothiadiazine-S,S-dioxide and congeners. Other AMPA receptor agents or drugs are expected to be developed.

Turning now to the subject methods, in the subject methods, a therapeutically effective amount of one or more, usually no more than 5, more usually no more than 2, types of distinct ampakine compounds, as described above, are administered to a mammalian host in which modulation of the endocrine system is desired. The term "therapeutically effective amount" means an amount effective to cause a modulation or alteration in the endocrine system of the host being treated, usually by changing the blood levels of one or more particular hormones.

The compounds of this invention can be incorporated into a variety of formulations for therapeutic administration, i.e. combined with a physiological acceptable vehicle to produce a pharmaceutical composition. Examples of suitable pharmaceutical compositions include capsules, tablets, syrups, suppositories, and various injectable forms. Administration of the compounds can be achieved in various ways, including oral, bucal, rectal, parenteral, intraperitoneal, intradermal, transdermal administration. Preferred formulations of the compounds are oral preparations, particularly capsules or tablets.

Dose levels can vary as a function of the specific compound, the severity of the symptoms, and the susceptibility of the subject to side effects. Some of the specific compounds that stimulate glutamatergic receptors are more potent than others. Preferred dosages for a given compound are readily determinable by those of skill in the art by a variety of means. A preferred means is to measure the physiological potency of a given compound that is a candidate for administration, by the method of Davis et al., "A profile of the behavioral changes produced by the facilitation of AMPA-type glutamate receptors," (Psycopharmacology, 1997 (in press)). Briefly, glutamate induced currents in excised patches and excitatory synaptic responses are measured in the presence of different concentrations of test compounds, and the differences in dosage response potency are recorded and compared Davis et al. found that one specific compound designated BDP-20 was about ten-fold more potent than another designated BDP-12 in a variety of behavioral (exploratory activity, speed of performance) and physical (excised patches and excitatory synaptic responses) tests. The relative physiological potency was an accurate measure of their behavioral potency. Thus, excised patches and excitatory synaptic responses may be used to gauge the relative physiological (and behavioral) potency of a given compound with regard to a known standard. Alternatively, the physiological potency of a given compound that is a candidate for administration can be evaluated by methods detailed in Staubli, U. et al., 1994a, *Proc. Natl. Acad. Sci. USA*, 91:777–781 and Arai et al., 1994, *Brain Res.*, 638:343–346. Briefly, currents in excised patches or from excitatory synaptic responses in hippocampal slice preparations are measured in the presence of different concentrations of test compounds, and the concentrations to achieve a standard response are determined and compared. A good correlation between physiological potency (increased AMPA currents) and behavioral effects (various learning paradigms) has been observed. Thus, AMPA current modulation in vitro may be used to gauge the relative potency of a given compound for a biological response.

The above described compounds and/or compositions are administered at a dosage sufficient to achieve the desired modulation of endocrine system while minimizing any side-effects. Typical dosages for systemic administration range from 0.1 to 10 milligrams per kg weight of subject per administration.

The dosing may be scheduled as desired, where a dose is administered periodically over a given period of time, e.g. once a day for a month or longer, twice a day on a daily basis for two weeks, and the like. For example, a typical dosage may be one 10–50 mg tablet taken once a day, or one time-release capsule or table taken once a day and containing a proportionally higher content of active ingredient. The time-release effect may be obtained by capsule materials that dissolve at different pH values, by capsules that release slowly by osmotic pressure, or by any other known means of controlled release.

The subject methods may be used to modulate the activity of the endocrine system, or subset or portion thereof, of a variety of different mammalian hosts. Mammalian hosts which may be treated according to the subject methods include rare and/or valuable animals, domestic animals, such as livestock, e.g. horses, cows, pigs, sheep, and the like; and pets, e.g. dogs, cats, and the like; and humans.

The term endocrine system as used in this application refers in general to the hormonal cell-cell communication system of the mammal. By modulation of the endocrine system is meant that the hormonal cell-cell communication of the mammal is altered in some manner, usually through a modulation or change in the blood circulatory level of one or more endogenous hormones, where modulation includes both increasing and decreasing the circulatory level of one or more hormones, usually increasing the circulatory level of one or more hormones, in response to the administration of the ampakine compound. Usually the subject methods are employed to modulate the activity of a particular hormonal system of the endocrine system of the mammal, where hormonal systems of interest include those which comprise glutamatergic regulation, particularly AMPA receptor regulation, where the hypothalamus-pituitary hormonal system is of particular interest.

Within the hypothalamus-pituitary system, of interest is the modulation of the following pairs of hypothalamic and related pituitary hormones: GHRH and GH; LHRH and LH/FSH, CRF and ACTH, and the like.

The subject methods find use in a variety of diverse applications where one wishes to modulate a mammalian endocrine system. Representative applications in which the subject methods find use include the treatment of diseases associated with or resulting from the dysfunction of the endocrine system, where dysfunction refers to hyper or hyposecretion of one or more specific hormones, usually hyposecretion of one or more hormones. The terms "treatment," "treating," and "treat" and the like are used herein to generally mean obtaining a desired pharmacology and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" therefore includes: (a) preventing the disease or symptom from occurring in a subject which may be predisposed to the disease or symptom but has not yet been diagnosed as having the disease or symptom; (b) inhibiting the disease symptom, i.e. arresting its development; or (c) relieving the disease symptom, i.e. causing regression of the disease or symptom.

Of particular interest is use of the subject methods to treat diseases associated with dysfunction of the hypothalamus-pituitary hormonal system, where the dysfunction of this particular system results in the hyposecretion of one or more pituitary hormones, where the pituitary hormones are usually under the regulatory control of a neuropeptide secreted by the hypothalamus, particularly a neuropeptide secreted in response to binding of glutamate to an AMPA receptor of the hypothalamus.

Of particular interest is use of the subject methods to upregulate the production of endogenous hormone by the pituitary, where disease has resulted in a down regulation of hormone production by down regulating the production of the requisite hypothalamic stimulatory hormone. Thus, in this class of diseases, by administering ampakine comprising pharmaceutical compositions to the host, one upregulates the production of the stimulatory hypothalamic neuropeptide, which in turn upregulates the production of endogenous hormone by the pituitary, thereby increasing the circulatory levels of the hormone in the host.

Accordingly, one class of diseases which may be treated according to the subject methods are diseases associated with hyposecretion of growth hormone, resulting in abnormally low circulatory levels of growth hormone in the mammal, where the hyposecretion is not the result of substantially complete failure in the capability of the pituitary to produce growth hormone. By treating is meant that the subject methods result in an elevated circulatory level of growth hormone compared to the level prior to treatment.

One "disease" characterized by such down regulation of endogenous growth hormone production is aging. Therefore, the subject methods find use in the treatment of symptoms associated with aging, such as reduction in lean body mass, bone, muscle and the like. Other diseases associated with depressed blood circulatory growth hormone levels which may be treated by the subject methods include hyposomatotropism resulting from tumors, trauma, infections, and the like.

The following examples are offered by way of illustration and not by way of limitation.

EXPERIMENTAL

I. The Use of Positive Modulators of AMPA Type Glutamate Receptors Upregulate Hormonal Secretions: Growth Hormones Experiments were conducted to assess whether the secretion of growth hormone (GH) could be upregulated through positive, allosteric modulation of AMPA receptors. The influence of GR87 (see Compound 25, supra), a member of the Ampakine class of AMPA receptor-modulatory drugs, on GH control was characterized at two points along the neuroendocrine axis: 1) serum levels of GH; and 2) secretion of the GH-releasing hormone (GHRH) from the hypothalamus. A summary of the data gathered in these experiments follows, along with a brief description of the experimental design.

A. Determination of serum levels of GH following prolonged administration of GR87

Figure 2:
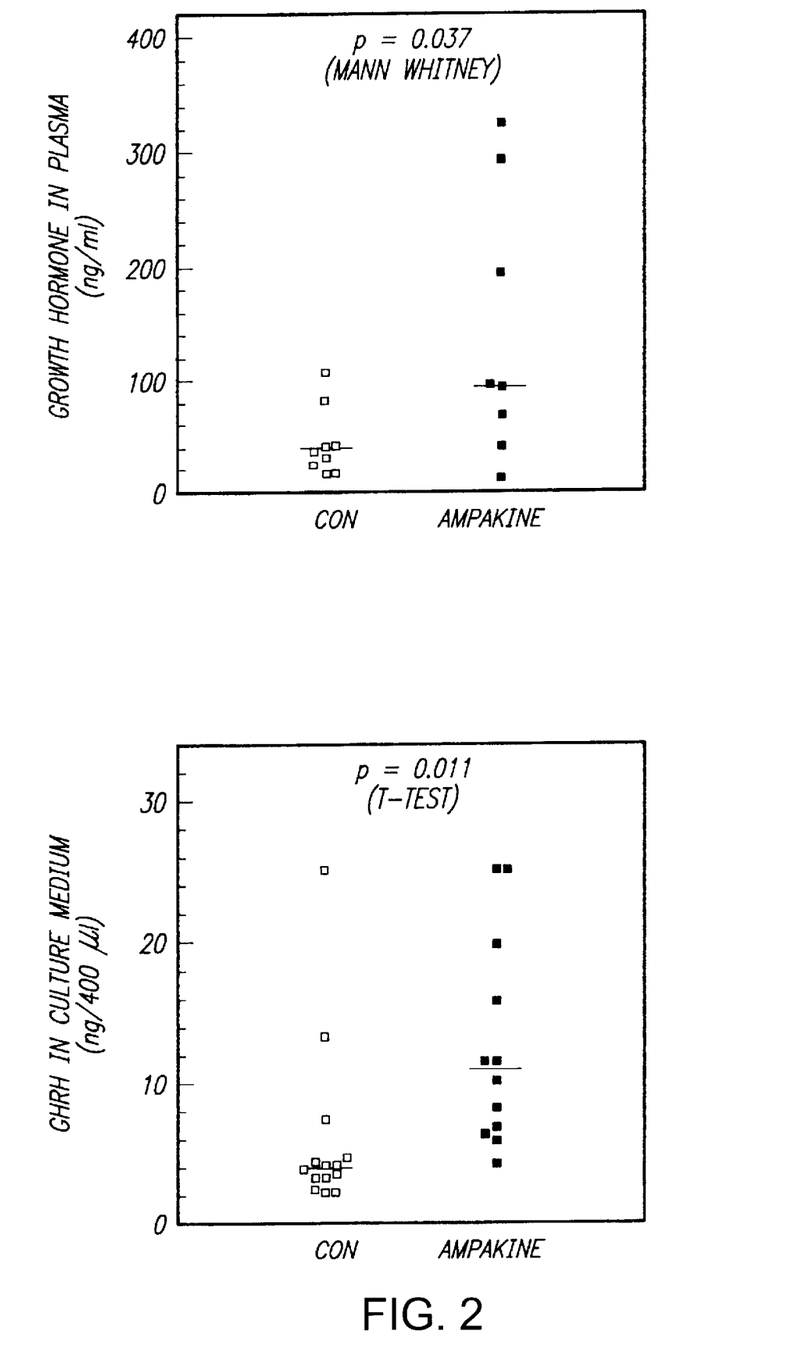
FIG. 2 provides a graphical representation of the effects of prolonged administration of GR87 on serum GH levels.

In this in vivo study, GH concentrations were analyzed in blood samples taken from rats that had received daily administration of the GR87 for a week. One group of rats were given GR87 via their water supply on a daily basis at a concentration of 4 mM. Access to water was restricted to 25 min per day (beginning at 10:30 am) so that a large volume (and thus drug dosage) would be consumed. After 7 to 8 days, blood was drawn from drug-treated and control rats at 11:30 am, 12:30 pm, and 1:30 pm. Blood samples were centrifuged and GH levels in the cleared serum were determined using a radioinmmunbassay kit. Two animals were implanted with osmotic minipumps containing the ampakine LN1, (see Compound 14, supra), allowing for direct and continuous application of the drug into the cerebral ventricles for a period of 7 days. The results of the study are summarized in FIG. 2. As shown, the mean value of growth hormone in the blood for nine control rats was less than half the mean value for a group of eight rats that received an ampakine. This effect was in the predicted direction and was statistically significant. (p=0.037).

B. In Vitro Analysis of the Effects of an Ampakine on the Release of Growth Hormone Releasing Hormone (GHRH)

Figure 3:
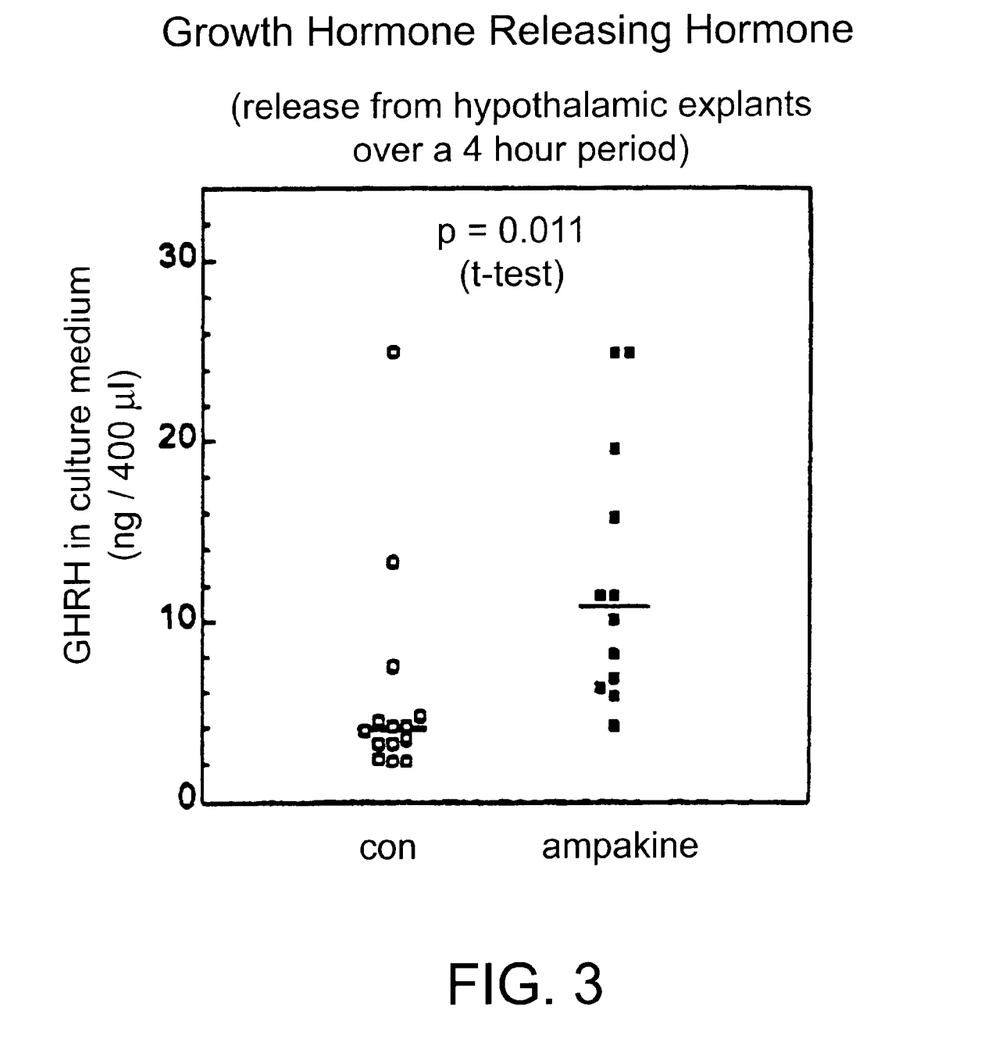
FIG. 3 provides a graphical representation of the effects of GR87 exposure on the secretion of GHRH by hypothalamic cells in culture.

The arcuate nucleus of the hypothalamus contains the majority of cells that synthesize GHRH and secrete the releasing factor into the anterior pituitary. Sections of the hypothalamus containing the arcuate nucleus were explanted from postnatal day 10–12 rats and maintained in static culture. Once established, these cultures were used to test the prediction that positive, allosteric modulators of AMPA type glutamate receptors will increase the release of GHRH from the hypothalamus into the culture medium. Explants were exposed to GR87 at 100 $\mu$m for four hours on some days and to vehicle for the same period on other days. Concentrates of the media were prepared following the exposure periods of GHRH assayed using a commercially available kit. Using a within culture design, i.e. drug vs. vehicle in the same tissue well, provided a control for differences in tissue thickness and the extent to which the arcuate was contained within the explants. The results of the study are summarized in FIG. 3. As shown, the amount of GHRH in the media was about threefold greater after four hours of treatment with ampakine than it was after an equivalent period of vehicle application. This effect was in the predicted direction and was statistically significant (p=0.011).

A single experiment was conducted to test if prolonged administration of GR87 at 100 μm would affect GHRH secretion. A group of 12 explants was exposed to the modulator for 24 hours and a second set treated with vehicle for the equivalent period. The media level of GHRH for the ampakine treated explants was 47 ng/400 μl while that for the controls was 18 ng/400 μl.

It is evident from the above results and discussion that novel methods of conveniently regulating the endocrine system of a mammal are provided. Since the subject methods employ small, synthetic organic compounds, they do not suffer from the problems associated with delivery of larger peptide compounds, where, depending on the method of their production and physical characteristics, such compounds may be contaminated with various pathogens, require invasive administration, or suffer from other disadvantages. Furthermore, since the subject methods modulate the endocrine system through regulation of endogenous hormonal production, the possibility exists to achieve better regulation of the endocrine system than is obtainable with convention hormonal replacement therapy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for increasing the circulatory level of growth hormone in a mammalian host, the method comprising:

administering to the host an ampakine, wherein the ampakine is a positive allosteric modulator of an AMPA receptor of the hypothalamus;

whereby the circulatory level of growth hormone in the mammalian host increases.

2. The method according to claim 1, where the mammalian host is a human.

3. The method according to claim 1, wherein the mammalian host is suffering from a disease associated with an abnormally low circulatory level of growth hormone.

4. The method according to claim 3, wherein the disease is associated with an age related decrease in a circulatory level of growth hormone.

5. The method according to claim 1, wherein said administering is by oral delivery.

6. The method according to claim 5, wherein the ampakine is a compound of the formula:

wherein:

$R^1$ is N or CH;

m is 0 or 1;

$R^2$ is $(CR^3{}_2)_{n-m}$ or $C_{n-m}R^3{}_{2(n-m)-2}$, in which n is 4, 5, or 6, and the $R^3$'s in any single compound are the same or different;

wherein:

each $R^3$ is H or $C_1$–$C_6$ alkyl, or one $R^3$ is combined with $R^4$ to form a single bond linking the no. 6 and no. 3' ring vertices or to form a single divalent linking moiety linking the no. 6 and no. 3' ring vertices, any remaining $R^3$'s being H or $C_1$–$C_6$ alkyl, or one $R^3$ is combined with $R^5$ to form a single bond linking the no. 2 and no. 3' ring vertices or to form a single divalent linking moiety linking the no. 2 and no. 3' ring vertices, any remaining $R^3$'s being H or $C_1$–$C_6$ alkyl, wherein the linking moiety in the $R^3$ definitions is $CH_2$, O, NH or $N(C_1$–$C_6$ alkyl);

$R^4$ when not combined with any $R^3$ is H, $C_1$–C6 alkyl or $C_1$–$C_6$ alkoxy;

$R^5$ when not combined with any $R^3$ is H, $C_1$–$C_6$ alkyl, or $C_1$–$C_6$ alkoxy;

$R^6$ is H, OH, $C_1$–$C_6$ alkyl, $C_1$–$C_6$ alkoxy, hydroxy-($C_1$–$C_6$ alkyl), or $C_1$–$C_6$ alkoxy-($C_1$–$C_6$ alkyl), or is combined with $R^7$;

$R^7$ is H, OH, $C_1$–$C_6$ alkyl, $C_1$–$C_6$ alkoxy, hydroxy-($C_1$–$C_6$ alkyl), $C_1$–$C_6$ alkoxy-($C_1$–$C_6$ alkyl), amino, mono($C_1$–$C_6$ alkyl)amino, or di($C_1$–$C_6$ alkyl)amino, or is combined with $R^6$; wherein $R^6$ and $R^7$ when combined form one of the following:

wherein:

$R^8$ is O, NH or $N(C_1$–$C_6$ alkyl);

$R^9$ is O, NH or $N(C_1$–$C_6$ alkyl); and the $R^{10}$'s in any single compound are the same or different, and each $R^{10}$ is H or $C_1$–$C_6$ alkyl, wherein p is 1, 2, or 3, and q is 1 or 2.

7. The method according to claim 5, wherein the ampakine is of the formula:

8. The method according to 5, wherein the ampakine is of the formula:

* * * * *